United States Patent
Tressler

(12) 
(10) Patent No.: US 6,720,873 B1
(45) Date of Patent: Apr. 13, 2004

(54) METHOD AND APPARATUS FOR TESTING MAGNETIC PROXIMITY DETECTORS ON SKI LIFTS

(76) Inventor: Brett D. Tressler, 704 Sterner St., Confluence, PA (US) 15424

( * ) Notice: Subject to any disclaimer, the term of this patent is extended or adjusted under 35 U.S.C. 154(b) by 0 days.

(21) Appl. No.: 10/377,554

(22) Filed: Mar. 3, 2003

(51) Int. Cl.[7] .......................... G08B 29/00; B61B 11/00
(52) U.S. Cl. ...................... 340/515; 340/396; 340/673; 340/677; 340/686.2; 340/686.6; 200/61.18; 104/173.2; 104/192; 324/228
(58) Field of Search .................. 340/515, 547, 340/548, 568.2, 564, 596, 673, 665, 668, 676, 677, 686.1, 686.2, 686.3, 686.6; 200/61.18, 61.13; 104/173.2, 180, 192, 307; 335/207; 324/228, 200, 207.2, 216

(56) References Cited

U.S. PATENT DOCUMENTS

| | | | |
|---|---|---|---|
| 4,096,437 A | * | 6/1978 | Kitzinger et al. ........... 324/227 |
| 4,271,763 A | | 6/1981 | Berger ..................... 200/61.18 |
| 4,427,940 A | * | 1/1984 | Hirama et al. .............. 324/240 |

* cited by examiner

*Primary Examiner*—Donnie L. Crosland
(74) *Attorney, Agent, or Firm*—Carothers & Carothers

(57) ABSTRACT

A device for testing a cable deroped magnetic proximity detector positioned adjacent a cable sheave or sheave assembly on a cable operated ski lift. A sleeve of non-ferromagnetic material is temporarily secured coaxially over the steel lift cable and the sleeve is dimensioned in length and thickness in amounts sufficient to raise the cable simultaneously away from the detector and the adjacent sheaves whereby the detector indicates a derope condition. When the ski lift is operated to thereby move the sleeve over the detector and adjacent sheaves, a derope condition will be simulated and the alarm tested to determine whether it provides the appropriate signal.

9 Claims, 1 Drawing Sheet

METHOD AND APPARATUS FOR TESTING MAGNETIC PROXIMITY DETECTORS ON SKI LIFTS

FIELD OF THE INVENTION

This invention relates generally to electromagnetic proximity detectors and more particularly to devices for testing such magnetic proximity detectors which are used with ski lifts or tramways for detecting a derope condition of the cable utilized as a haul rope for the lift system.

BACKGROUND OF THE INVENTION

Magnetic proximity detectors are commonly used on ski lifts and tramways for detecting a derope condition of the steel cable used as a haul line or haul rope. An example of such a detector is illustrated in U.S. Pat. No. 4,271,763, issued on Jun. 9, 1981. This patent also discloses a testing device.

The testing device shown in this patent consists of a non-ferromagnetic sleeve which is provided in substantially symmetric halves which are fastened together with non-magnetic bolts over the lift cable. The sleeve is relatively thin so as not to significantly raise the cable away from the detector when riding thereover and the sleeve is further provided with circular shaped magnets which are positioned in two circumferential rows and the permanent magnets are chosen and positioned to form a north pole and a south pole so as to disrupt and modify the electromagnetic field of the detector when passing thereover to send a derope detector signal for testing the electromagnetic detector.

While this test device is effective, it is nevertheless difficult and expensive to manufacture and depends upon the attached permanent magnets not becoming dislodged from the sleeve.

It is accordingly an object of the present invention to provide such a safety testing device for electromagnetic proximity detectors used on ski lifts and tramways which is devoid of these mentioned problems or inadequacies.

SUMMARY OF THE INVENTION

The apparatus of the present invention is provided for testing a cable derope magnetic proximity detector which is positioned adjacent a cable sheave or sheave assembly on a cable operated ski lift. The testing apparatus is comprised of a non-ferromagnetic sleeve having an inner diameter for mating the outside diameter of the steel lift cable and is dimensioned in length and thickness in amounts sufficient to raise the cable simultaneously away from the detector and the adjacent sheave or sheave assembly whereby the detector will indicate a derope condition. The sleeve is flexible and preferably made of plastic, including hard rubber, and the sleeve is provided with tapered ends to provide an easy ride-up transition onto the sheaves. The sleeve is provided in two longitudinal split halves and may be readily secured in place over the cable with tape.

Accordingly, in order to test the magnetic proximity detectors, the sleeve is temporarily secured over the cable and the ski lift or tramway is operated to thereby move the sleeve with the cable over the detector and adjacent sheave or sheave assembly in order to simulate a derope condition and thereby cause the magnetic proximity detector to set off an alarm. By design, the testing device will raise the steel cable haul rope up off the sheave wheels of the sheave assembly to test the proximity switch of the magnetic proximity detector and it will also maintain the haul rope centered on the sheave wheels so that deropement does not occur during testing. Also, if the cable twists, it will not effect the testing device, as can be a problem with prior art testing devices.

BRIEF DESCRIPTION OF THE DRAWINGS

Other objects and advantages appear hereinafter in the following description and claims. The accompanying drawings show, for the purpose of exemplification, without limiting the scope of the invention or appended claims, certain practical embodiments of the present invention wherein:

DETAILED DESCRIPTION OF THE PREFERRED EMBODIMENT

Figure 1:
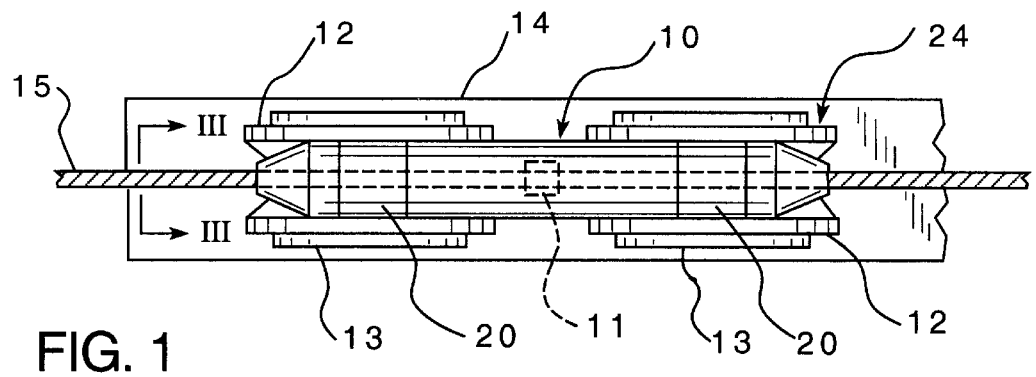
FIG. 1 is a plan view of a portion of a ski lift tower showing the testing apparatus of the present invention riding over a sheave assembly and underlying magnetic proximity detector.

The testing apparatus 10 of the present invention is provided to test the operating condition of cable derope magnetic proximity detector 11 positioned adjacent cable sheaves 12 mounted for rotation on sheave assembly blocks 13 of sheave assembly 24, which in turn are secured to the upper surface of ski lift tower arm bracket 14 which is elevated far above an underlying ground surface (not shown). The ski lift is of a conventional type operated by a haul rope or line in the form of a steel cable 15 which carries the ski lift chairs (not shown).

Figure 2:
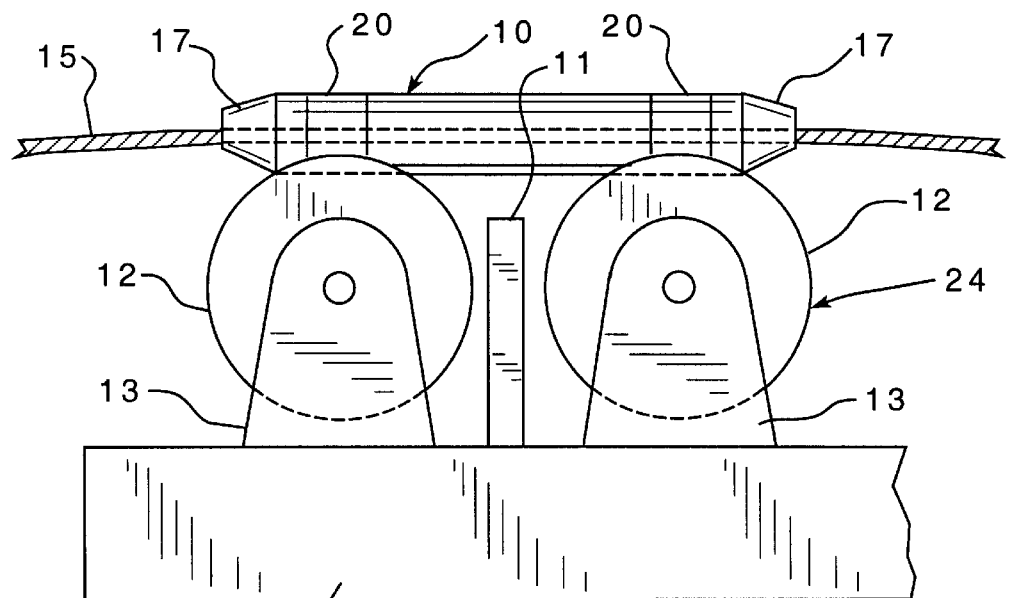
FIG. 2 is a view in side elevation of the apparatus shown in FIG. 1.
Figure 3:
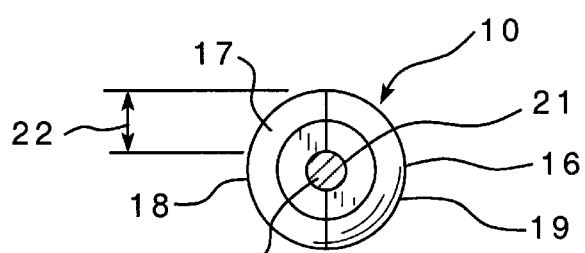
FIG. 3 is a sectional end view of the testing apparatus of the present invention as separated from the sheave assembly shown in FIGS. 1 and 2 and as seen along section line III—III.

The testing apparatus 10 includes a non-ferromagnetic sleeve 16 which is constructed of plastic and has tapered ends 17 so that the sleeve 16 will easily ride up into the groove surfaces of sheaves 12 without deroping. The sleeve 16 is provided in two longitudinal split halves 18 and 19 and the two halves are secured snugly over top of cable 15 with the use of tape 20. Non-ferromagnetic sleeve 16 is provided with an inside diameter 21 for mating the outside diameter of the cable 15 and the sleeve 16 is further dimensioned in overall length and thickness 22 in amounts sufficient to raise the cable 15 simultaneously away from detector 11, as is best illustrated in FIG. 2, and the adjacent sheave or sheaves 12 of sheave assembly 24 whereby the electromagnetic proximity detector 11 will indicate a derope condition and set off the conventional alarm (not shown) connected to the detector.

The plastic sleeve 16 is composed of plastic, which may include hard rubber, and is therefore sufficiently flexible to ride up onto the sheaves 12 without causing an actual derope condition.

I claim:

1. The method of testing a cable derope magnetic proximity detector positioned adjacent a cable sheave on a cable operated ski lift comprising:

temporarily securing a sleeve of non-ferromagnetic material to and coaxially over the cable, said sleeve dimensioned in length and thickness an amount sufficient to raise said cable simultaneously away from said detector and said adjacent sheave whereby said detector indicates a derope condition, and operating the ski lift to thereby move said sleeve over said detector and adjacent sheave.

2. The method of claim 1, wherein said sleeve is flexible.

3. The method of claim 2, wherein said sleeve is plastic.

4. The method of claim 1, wherein said sleeve has tapered ends.

5. An apparatus for testing a cable derope magnetic proximity detector positioned adjacent a cable sheave on a cable operated ski lift, said apparatus comprising:

a non-ferromagnetic sleeve having an inside diameter for mating the outside diameter of the cable and dimensioned in length and thickness an amount sufficient to raise said cable simultaneously away from said detector and said adjacent sheave whereby said detector will indicate a derope condition, and means for temporarily securing said sleeve to and coaxially about said cable.

6. The apparatus of claim 5, wherein said sleeve is flexible.

7. The apparatus of claim 6, wherein said sleeve is plastic.

8. The apparatus of claim 5, wherein said sleeve has tapered ends.

9. The apparatus of claim 5, wherein said means includes said sleeve comprised of longitudinal split halves and tape securing said halves together.

\* \* \* \* \*